United States Patent
Cavdar

[19]

[11] Patent Number: 6,094,967
[45] Date of Patent: Aug. 1, 2000

[54] TRIBOMETER

[75] Inventor: Bulent Cavdar, Wheaton, Ill.

[73] Assignee: BorgWarner Inc., Troy, Mich.

[21] Appl. No.: 09/081,524

[22] Filed: May 19, 1998

[51] Int. Cl.[7] .................................................. G01N 19/02
[52] U.S. Cl. ........................................................... 73/9
[58] Field of Search ............................................. 73/9, 10

[56] References Cited

U.S. PATENT DOCUMENTS

| | | | |
|---|---|---|---|
| 3,444,720 | 5/1969 | Link | 73/9 |
| 3,451,253 | 6/1969 | Happold | 73/9 |
| 3,648,511 | 3/1972 | Groat et al. | 73/9 |
| 3,717,025 | 2/1973 | Kronenberg et al. | 73/9 |
| 4,051,713 | 10/1977 | Bao et al. | 73/9 |
| 4,234,063 | 11/1980 | Blake | 188/181 T |
| 4,939,922 | 7/1990 | Smalley et al. | 73/10 |
| 5,107,448 | 4/1992 | Nash | 73/9 X |
| 5,259,236 | 11/1993 | English | 73/9 |
| 5,319,953 | 6/1994 | Germain et al. | 73/9 |
| 5,331,839 | 7/1994 | Schmidt | 73/9 |
| 5,490,410 | 2/1996 | Markstrom | 73/9 |
| 5,501,097 | 3/1996 | Nomura | 73/9 |
| 5,576,478 | 11/1996 | Brungraber | 73/9 |
| 5,734,088 | 3/1998 | Gunderson | 73/9 |
| 5,907,090 | 5/1999 | Gunderson | 73/9 |

*Primary Examiner*—Thomas P. Noland
*Attorney, Agent, or Firm*—Emch, Schaffer, Schaub & Porcello; Greg Dziegielewski

[57] ABSTRACT

The invention is directed to an improved tribometer used to measure and test the interactions of two sliding bodies. The tribometer includes a sliding unit for holding the test samples, a unit for reciprocating a test sample, a signal conditioning unit for receiving a plurality of signals from sensors and a data acquisition and control unit which receives the signal data and sends control instructions to the sliding unit and to the reciprocating unit.

15 Claims, 7 Drawing Sheets

TRIBOMETER

BACKGROUND OF THE INVENTION

Tribometers are well known in the art and are used to measure and test the interactions of two sliding bodies. For example, a tribometer can be used to measure and test materials which are used in brake linings. The present invention relates to an improved tribometer.

Some of the problems which must be addressed in an improved tribometer are the following:

1. The in situ observation of the physical and chemical changes at the interface of two sliding bodies by means of chemical and optical microscopy.

2. The relationship between friction phenomena and real contact area under various operating conditions.

3. The investigation of direct contacting asperities and load shared by lubricant film and asperities in boundary lubrication.

4. Investigation of real contact areas and junction growth in dry sliding.

5. Observation of oil film formation between the sliding bodies in eleastohydrodynamic lubrication.

6. The determination of surface elasticity of paper materials.

7. The studies of pore structures of porous materials and oil and air pockets development.

8. The study of break-in mechanisms and boundary film formations.

9. Contact temperature studies.

10. The study of stick-slip phenomena.

11. The study of the effects of system stiffness on friction and vibration phenomena.

12. The study of friction and wear mechanisms of dry and lubricated sliding bodies.

13. The study of friction and wear mechanisms of any kind of solid materials and surface coatings.

14. The study of lubricating properties of liquid and solid lubricants, greases and additives.

15. The study of friction and wear tests in controlled humidity environments.

The primary purpose of the present invention is to produce an improved tribometer which solves many of the problems in the art.

SUMMARY OF THE INVENTION

The present invention relates to an improved tribometer having a sliding unit for receiving test samples. A reciprocating drive unit is mounted adjacent the sliding unit and reciprocates a test specimen. A signal conditioning unit receives the signals from a plurality of sensors. A data acquisition and control unit obtains data from the signal conditioning unit and sends control instructions to the sliding unit and to the reciprocating drive unit.

DETAILED DESCRIPTION OF THE PREFERRED EMBODIMENT

Figure 5:
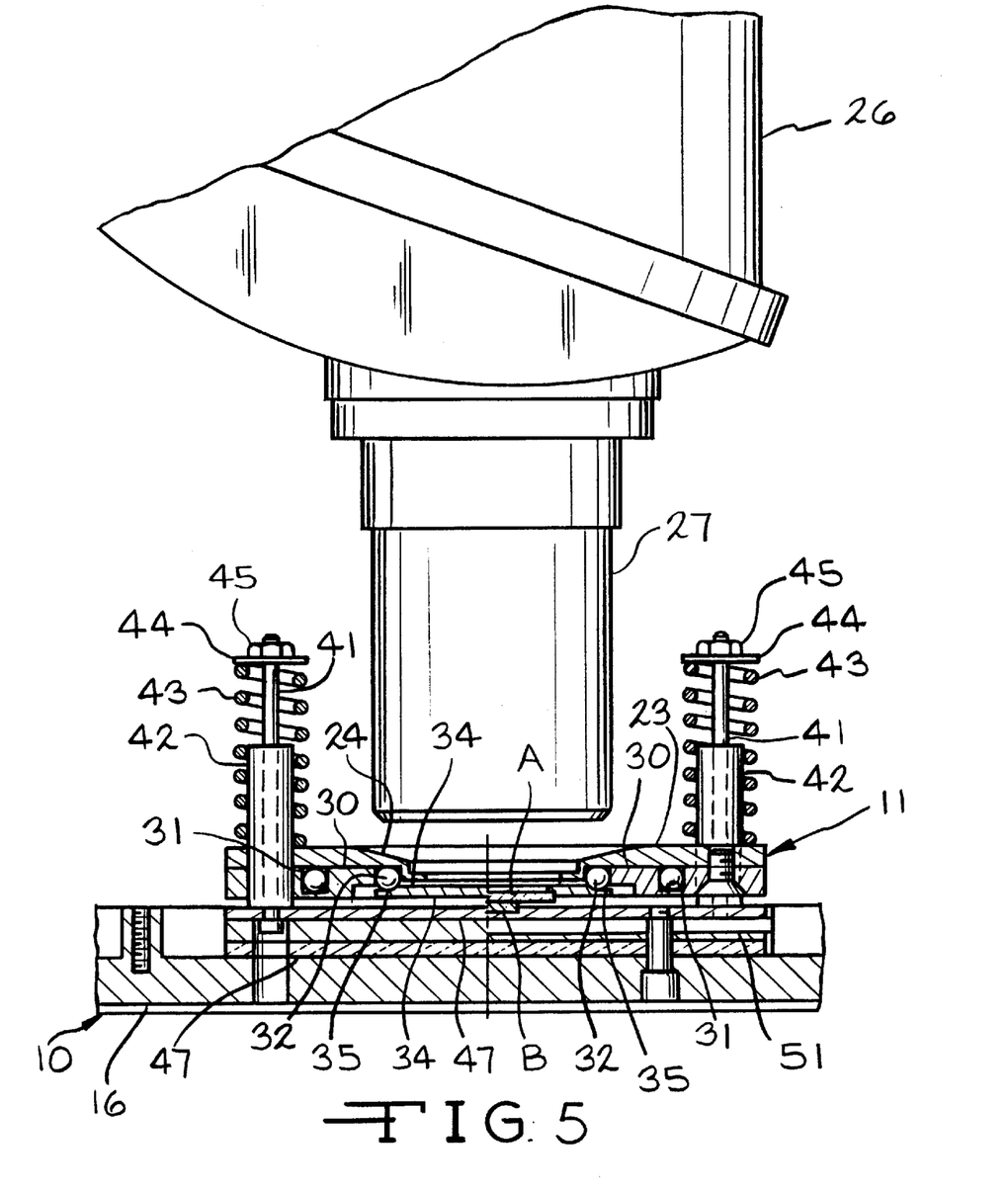
FIG. 5 is an enlarged cross-sectional view taken along the line 5—5 of FIG. 1 and showing a portion of a microscope.

Referring to the drawings, a tribometer according to the present invention is generally indicated by the reference number 10. The tribometer 10 can be operated as a stand alone friction and wear tester or with an optical and chemical microscope, as shown in FIG. 5. The tribometer 10 includes a sliding unit 11, a reciprocating motion drive unit 12, a signal conditioning unit 13 and a data acquisition and control unit 14.

Figure 1:
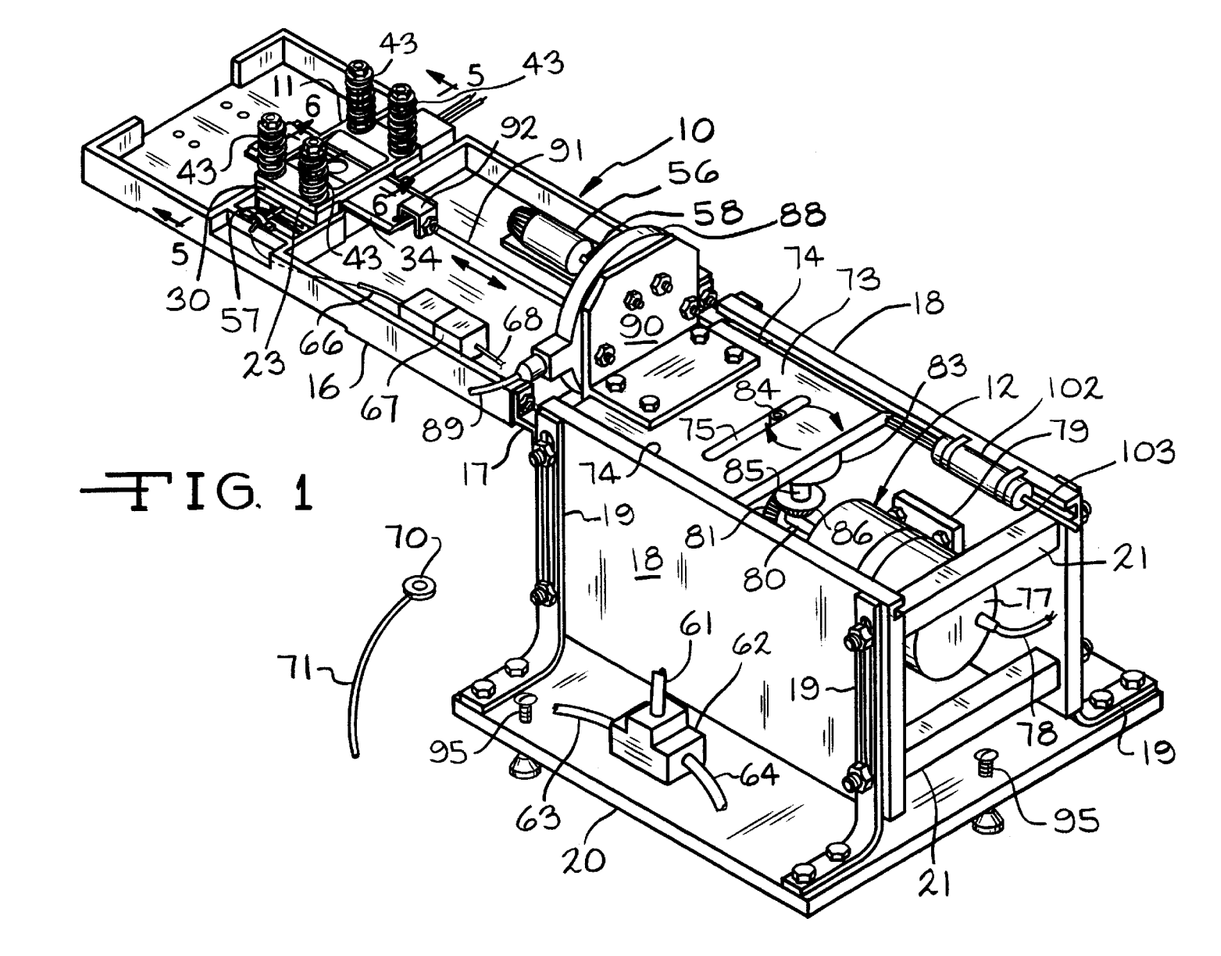
FIG. 1 is a perspective view of a tribometer, according to the present invention.

Referring to FIG. 1, the tribometer 10 includes a longitudinally extending rectangular base 16 which mounts the sliding unit 11. The base 16 is mounted by brackets 17 to a pair of spaced walls 18. The spaced walls 18 are vertically adjustably mounted by adjusting brackets 19 to a horizontal support member 20. Cross members 21 extend between the spaced walls 18 in this embodiment. The reciprocating motion drive unit 12 is mounted within the spaced walls 18.

The sliding unit 11 is thin and narrow in order to fit in the space between the stage and the nosepiece of various microscopes. Referring to FIGS. 1, 5, 6 and 7, the sliding unit 11 includes an upper plate 23 having a recess 24. As shown in FIG. 5, when a microscope 26 is used with the tribometer 10, a nose piece 27 of the microscope 26 is positioned adjacent the upper plate 23 and its recess 24. The upper plate 23 also includes a central opening 28. A pair of opposed and spaced bearing assemblies 30 defining races 31 for receiving a plurality of ball bearings 32 are mounted beneath the upper plate 23. An upper sample holder 34 having a pair of opposed bearing edges 35 is slideably mounted below the upper plate 23 such that the bearing edges 35 engage the ball bearings 32. The upper sample holder 34 includes a viewing window 36. The upper sample holder 34 mounts a test sample along its bottom surface. The upper sample holder 34 includes slots 37 at its opposed ends. The slots 37 are used to operatively connect the upper sample holder 34 to the reciprocating motion drive unit 12. The upper test sample is normally adhered to the bottom face of the upper sample holder 34. A lower sample holder 39 is positioned below the upper sample holder 34 and serves as a retainer for the lower test sample. The lower sample holder 39 includes a slot 40 for mounting a thermocouple sensor and a sample recess 54. Openings are provided in the corners of the lower sample holder 39 and the upper plate 23 to receive a plurality of screws 41. Bushings 42, coil springs 43, washers 45 and nuts 46 are mounted on the screws 41. The coil springs 43 provide the desired amount of spring forces or load to the aligned samples mounted on the upper sample holder 34 and the lower sample holder 39. The forces may be adjusted by adjusting the nuts 45 and also by removing the coil springs 43 and substituting other coil springs with different spring constants. The spring constant of the springs 43 are set precisely for studies such as system dynamics, friction and vibration, and stick-slip phenomenon.

Figure 7:
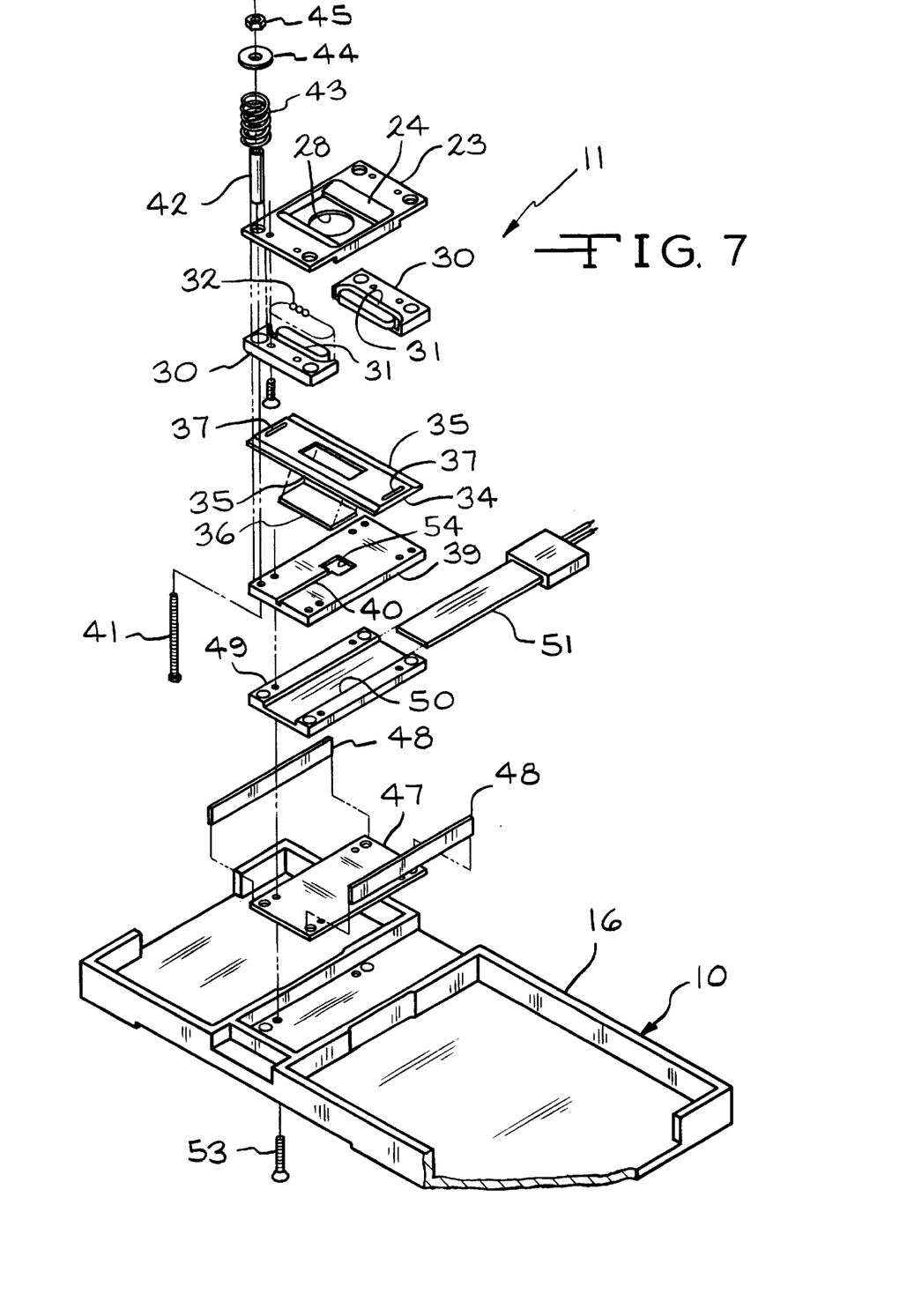
FIG. 7 is an exploded view showing portions of the sliding unit.

In the present embodiment, a horizontal insulating member 47 is positioned on the base 16. A pair of spaced insulating side walls 48 extend upwardly from the insulating member 47. The insulating member 47 and the insulating side walls 48 receive a holder 49 having a central slot 50 for receiving a band heater 51. A plurality of screws 53 interconnect the base 16, the insulating member 47, the holder 49 and the lower sample holder 39. Preferably the insulating member 47 and the insulating side walls 48 are constructed of ceramic materials in order to reduce heat transfer.

The ball bearings 32 when in contact with the bearing edges 35 of the upper specimen holder 34 guide the specimen holder 34 during its reciprocating motion. Therefore, the load is transferred from the coil springs 43 to the upper plate 23 and downwardly to the upper sample holder 34 through the ball bearings 32.

Figure 6:
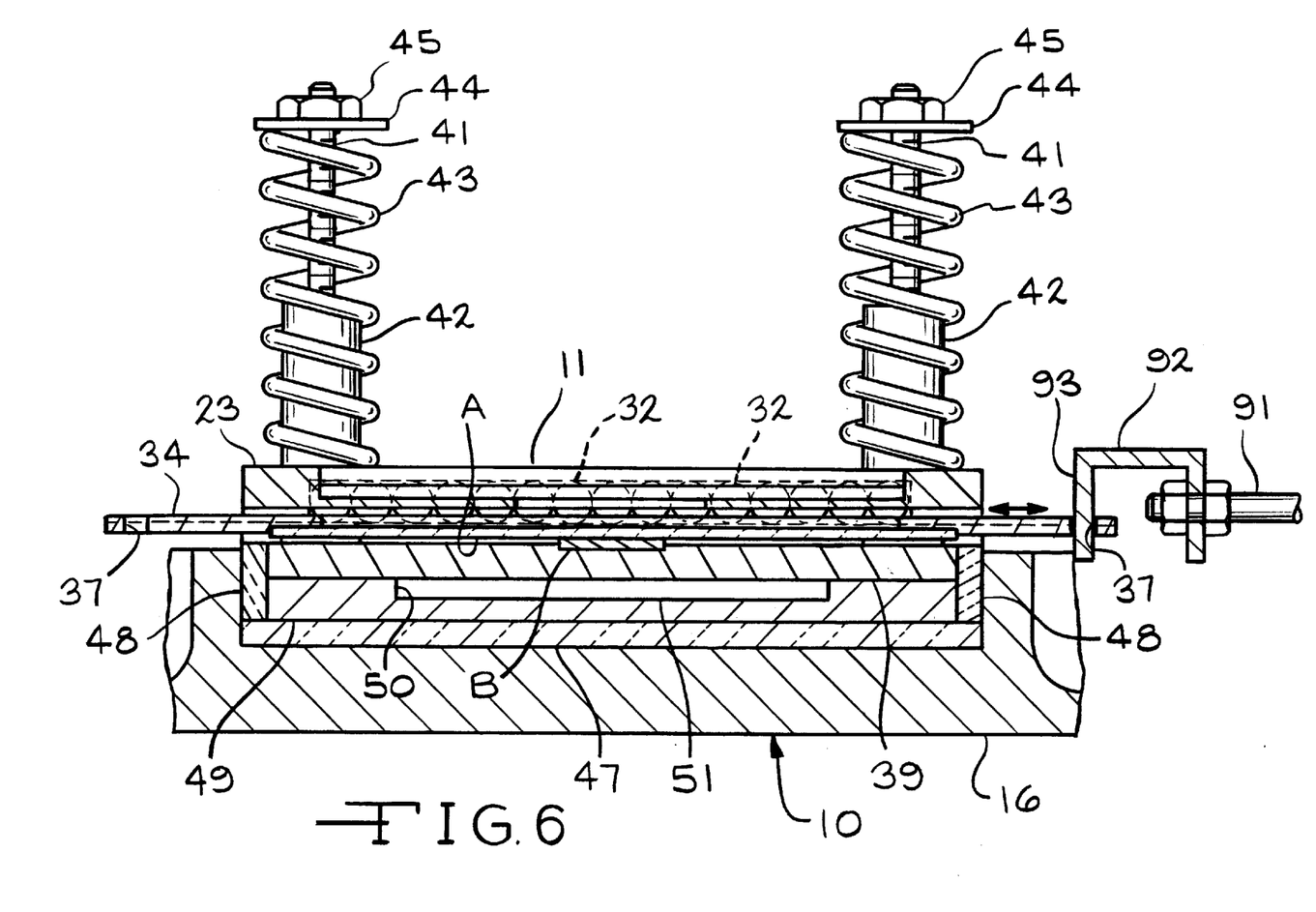
FIG. 6 is a cross-sectional along the lines 6—6 of FIG. 1.

Referring to FIG. 6, the sliding unit 11 is shown in its assembled position. An upper test sample A has been glued to the bottom face of the upper sample holder 34. The upper sample A is transparent when a microscope is used. The upper sample A is also flat. A lower test sample B is positioned in the sample recess 54 defined by the lower sample holder 39. The lower test sample B can be of any geometric shape.

The base 16 cantilevers from the walls 18. In addition to mounting the sliding unit 11, the base 1 6 mounts a humidity sensor 56. A thermocouple 57 is mounted in the slot 40 in the lower sample holder 39 (FIG. 7). The humidity sensor 56 is connected to a sensor conduit 58.

Figure 2:
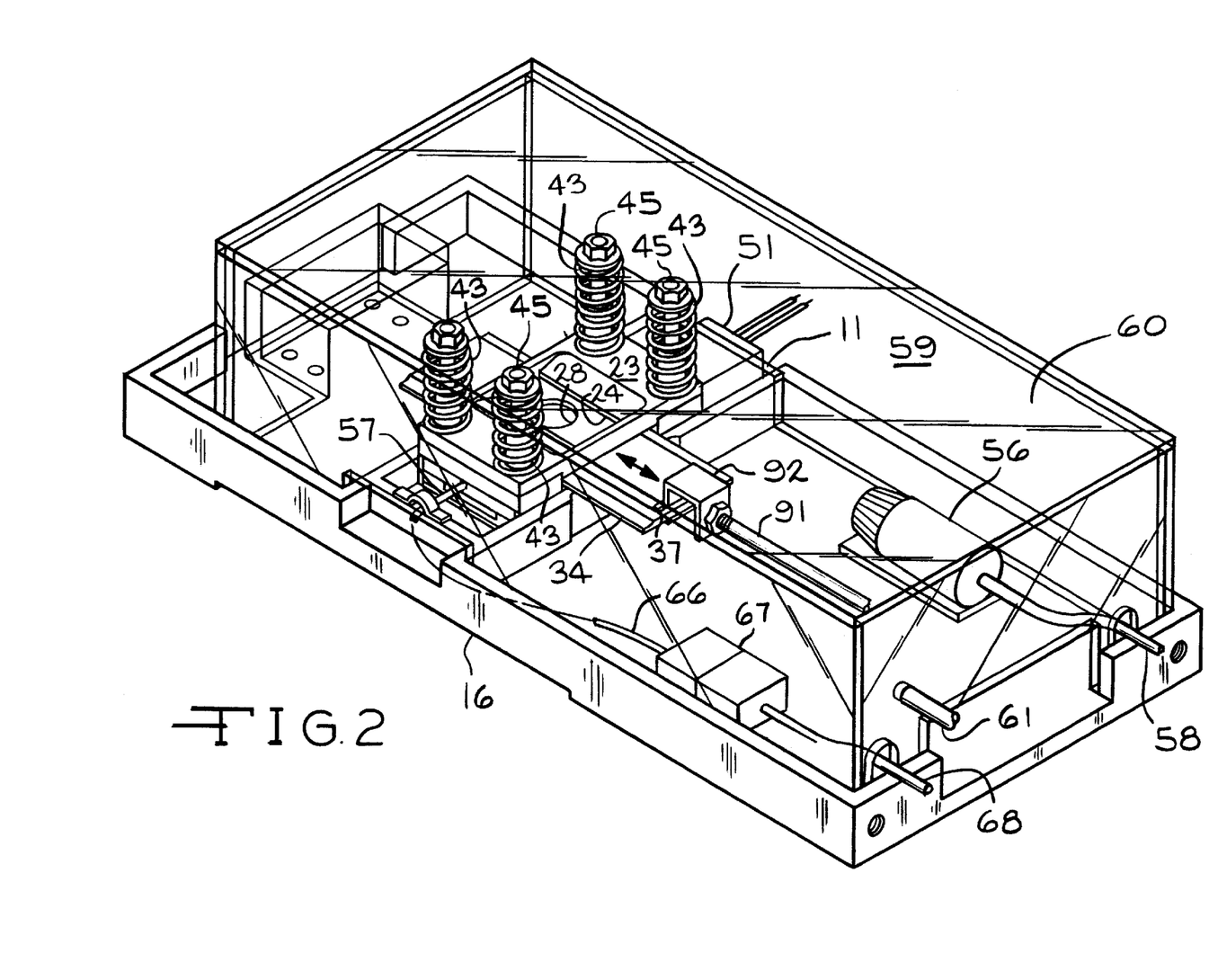
FIG. 2 is an enlarged perspective view of the sliding unit of the tribometer shown in FIG. 1 having a humidity chamber cover in place.
Figure 3:
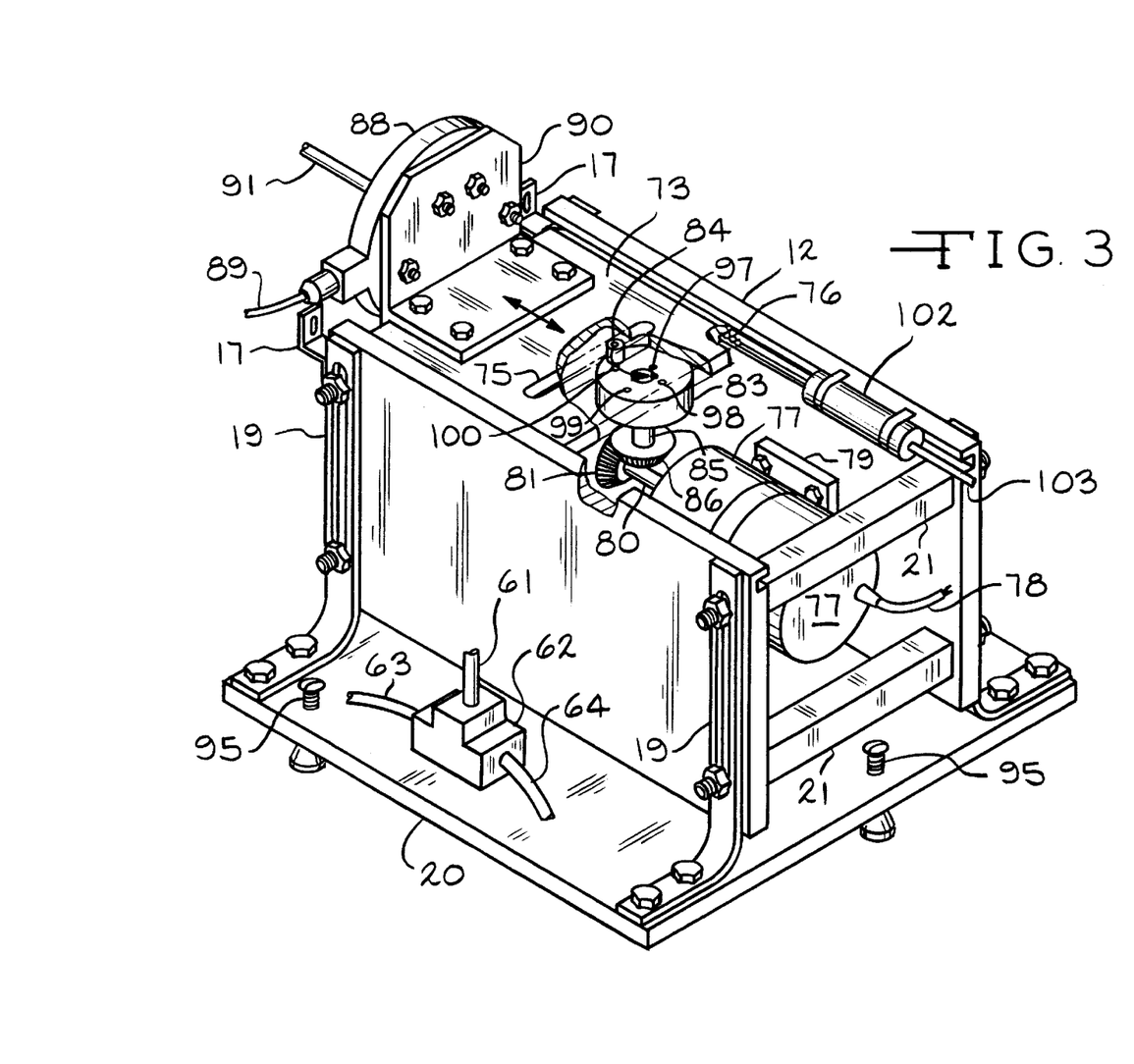
FIG. 3 is an enlarged perspective view of the reciprocating motion drive unit, shown in FIG. 1 and having portions broken away so the interior can be viewed.

Referring to FIG. 2, in a preferred embodiment, the base 16 mounts a transparent cover 59 which together with the base 16 defines a humidity chamber 60. A conduit 61 delivers gases to the humidity chamber 60 to provide the proper atmosphere. These gases include steam and nitrogen. Referring to FIG. 3, a solenoid valve 62 is mounted on the support member 20. The solenoid valve 62 is in communication with a steam inlet conduit 63 and a nitrogen inlet conduit 64. Depending on the predetermined demand, the conduit 61 is either supplied with no gas; steam through the steam inlet conduit 63, or nitrogen through the nitrogen inlet conduit 64.

The thermocouple 57 is electrically connected by a conduit or wire 66 through an electrical connecting block 67 to an electrical conduit 68. Referring to FIG. 1, a load sensor 70 which is operatively connected to a conduit 71 is placed under the lower sample B. The load sensor 70 is portable. It is held in place below the lower sample B for dynamic load measurements. It can be removed after the desired initial load is set, by adjusting the spring forces to reach the desired load on the samples A and B.

Referring to FIGS. 1 and 3, the reciprocating motion drive unit 12 is operatively connected to the upper specimen holder 34. A slide plate 73 is mounted for reciprocating movement in opposed slots 74 defined by the opposed walls 18. A plurality of ball bearings 76 are mounted in the slots 74 and ensure that the slide plate 73 rolls with negligible friction as it reciprocates. The slide plate 73 defines a cam slot 75 which is generally perpendicular to the walls 18. A DC variable speed electric motor 77 having a power input conduit 78 is mounted by brackets 79 to the walls 18. The electric motor 77 has a discharge shaft 80 which mounts a bevel gear 81. A crank disk 83 is mounted for rotation below the slide plate 73. On its upper surface, the crank disk 83 mounts a cam 84 which is positioned within the cam slot 75 of the slide plate 73. The crank disk 83 and the cam 84 are operatively connected by a shaft 85 and mating bevel gear 86 with the bevel gear 81 and the electric motor 77. When the motor 77 is activated, rotation of the mating gears 81 and 86 rotate the crank disk 83 which drives the cam 84. The cam 84 reciprocates the slide plate 73. A compression-tension load cell 88 having a sensing conduit 89 is positioned above the base 16 and is operatively mounted to the reciprocating slide plate 73 by a mounting bracket 90. A reciprocating shaft or rod 91 is connected at one end to the load cell 88 and is connected at the other end by a U-shaped bracket 92 to the upper specimen holder 34. A leg 93 of the U-shaped bracket 92 is received by one of the slots 37 of the upper sample holder 34.

A plurality of adjusting feet 95 are provided and act as a leveling mechanism which provides fine height and leveling adjustments to the horizontal support member 20 and the sliding unit 11 when the sliding unit 11 is placed under a microscope objective.

The frequency of the strokes of the rod 91 and the upper sample holder 34 is adjusted by adjusting the speed of the electric motor 77.

In the present reciprocating motion drive unit 12, the amplitude of the strokes of the rod 91 and the upper sample holder 34 can also be adjusted. As best shown in FIG. 3, the upper surface of the crank disk 83 defines four holes 97, 98, 99 and 100. The holes 97–100 have different radial spacings. The cam 84 is removably positioned in a selected one of the holes 97–100 depending on the amplitude of the stroke desired. As the radial position of the hole increases, the stroke of the upper sample holder 34 also increases.

A speed sensor 102 having a sensor output conduit 103 is mounted on a wall 18 of the reciprocating motion drive unit 12. In the present embodiment, the speed sensor 102 is operatively connected to and measures the velocity of the slide plate 73. In another embodiment (not shown) the speed sensor is mounted adjacent the sliding unit 11 and is operatively connected to the upper sample holder 34.

Figure 4:
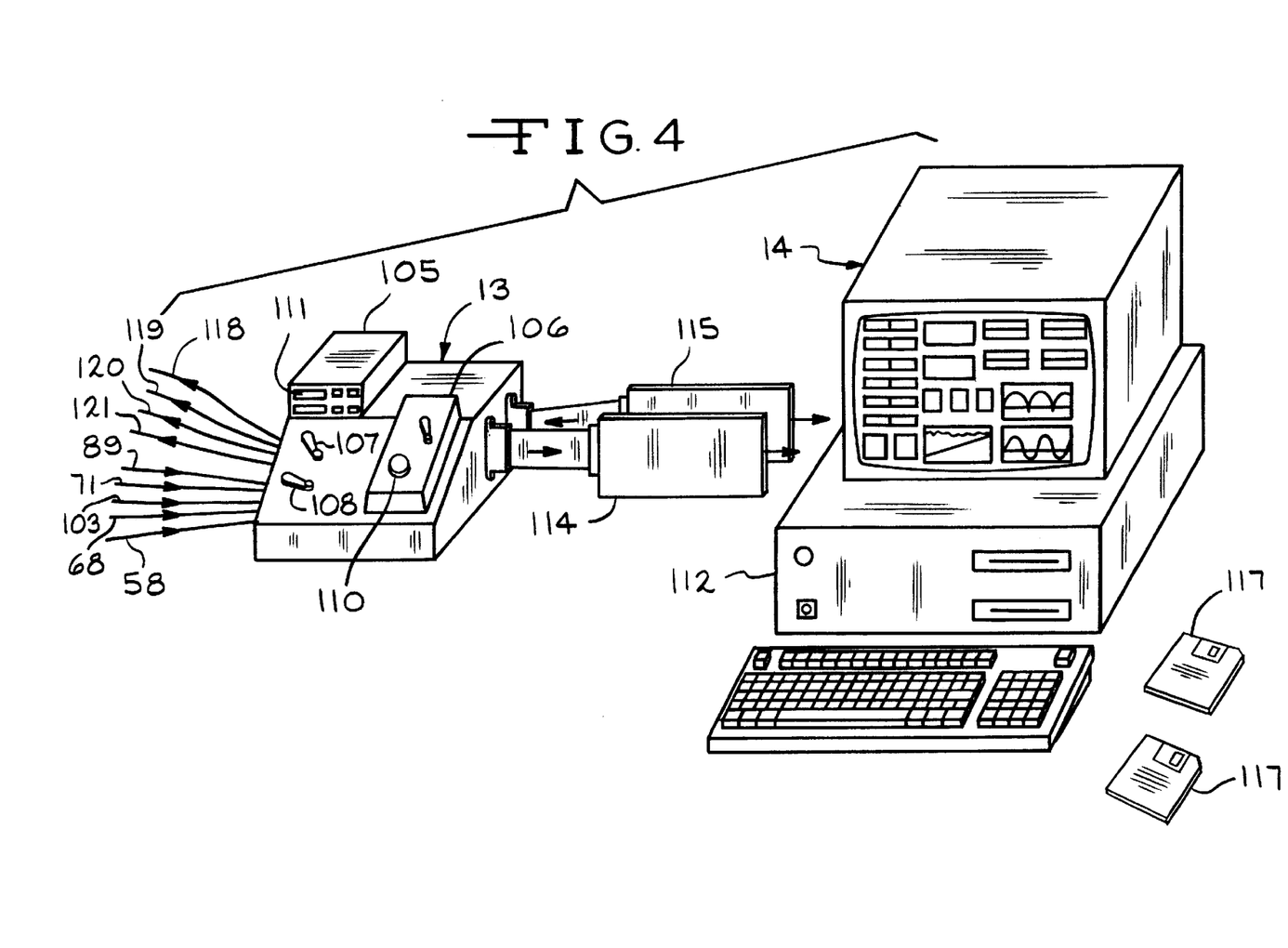
FIG. 4 is a perspective view showing the signal conditioning unit and the data acquisition and control unit of the tribometer.

Referring to FIG. 4, the signal conditioning unit 13 is illustrated. While any number of sensors may be operatively connected to the signal conditioning unit 13, in the present embodiment five sensors and sensor conduits are used. These include the load cell 88 and its sensing conduit 89, serving as a friction force sensor; the sensor conduit 71 which is connected to the load sensor 70 and is the normal load sensor under the lower sample B; the velocity sensor conduit 103 which is operatively connected to the speed or velocity sensor 102 and to the reciprocating slide plate 73 of the reciprocating motion drive unit 12; the sensor conduit 68 which is connected to the thermocouple 57 mounted on the sliding unit 11 in engagement with the lower sample B; and the sensor conduit 58 which is operatively connected to the humidity sensor 56 within the humidity chamber 60. The signal conditioning unit 13 amplifies and conditions the respective sensor signals before the signals are delivered to the data acquisition and control unit 14. The signal conditioning unit 13 includes a manual temperature controller 105 and a manual speed controller 106. A toggle switch 107 is connected to the temperature controller 105 and a toggle switch 108 is connected to the speed controller 106. The toggle switches 107 and 108 let the user select either manual or automatic computer control of temperature and speed. This is especially useful in the setting up of a new test.

The electric motor 77 is connected to the speed controller 106, which normally receives a set value for the speed from the control unit 14. If the toggle switch 108 has been moved to the manual position, the speed is set manually by a dial knob 110. The temperature controller 105 is in communication with the band heater 51. In the normal mode, temperature control is automatically provided by the computer 14. If the toggle switch 107 has been moved to the manual mode, temperature control is provided by a standard prior art programmable controller 111 which accepts a set point temperature input from the front panel of the temperature controller 105.

The data acquisition and control unit 14 includes two plug-in boards 114 and 115 and a computer 112. In the present embodiment the computer 112 is an IBM compatible computer. The plug-in board 114 is an analog to digital board with a plurality of input channels. In the present embodiment, the board 114 includes eight input channels. The plug-in board 115 is a digital to analog board and includes a plurality of control channels. In the present embodiment, the board 115 includes four control channels.

In the present embodiment, five of the input channels of the board 114 are utilized. These channels are operatively connected to: the load sensor 70; the speed or velocity sensor 102; the load cell 88; the thermocouple 57; and the humidity sensor 56. The remaining three channels are available for the future expansion of the data acquisition component.

In the present embodiment, the maximum sampling rate of the data acquisition board 114 is 100 kHz.

In the present embodiment, the four channels of the control board 115 are used for speed, temperature, humidity and video recording controls. After the output signals are processed by the control board 115 and are transmitted through the signal conditioning unit 13, an output speed control signal 118 is transmitted to the electrical motor 77. An output temperature control signal 119 is transmitted to the band heater 51. An output humidity control signal 120 is transmitted to the three-way solenoid valve 62. If a microscope having a digital camera and an image analysis station is utilized, an output triggering signal is transmitted to the video frame grabber of the image analysis station or to a VCR to record the images of the contact area in synchronism with the other tribometer recordings such as the contact forces, speed, temperature, humidity, etc.

User friendly, object orientated MS-Windows based application software 117 is used for a graphical user interface. The software is capable of doing data acquisition, control, analysis and presentation.

The data acquisition and control unit 14 also measures and controls the ambient humidity during testing. A steam generator is in communication with the steam conduit 63 and a dry nitrogen tank is in communication with the nitrogen conduit 64. The steam and nitrogen lines 63 and 64 are connected to the inlet ports of the three-way solenoid valve 62. The computer 112 compares the humidity reading generated from the humidity sensor 56 relative to the humidity set point and sends an on-off signal to the three-way solenoid valve. If a humidity control is not needed during tribotesting, the solenoid valve 62 is in the closed positioned and the cover 59 can be removed from the base 16. The data acquisition and computer control unit 14, in addition to humidity control, receives the conditioned and amplified signals by way of the A/D input board 114 and delivers controlling signals relating to motor speed, sample temperature, chamber and sample humidity together with VCR or video frame grabber controls through the D/A board 115, as discussed above.

Many revisions can be made to the above described embodiments without departing from the scope of the invention or from the following claims.

I claim:

1. An improved tribometer having a sliding unit for receiving test samples, a reciprocating motion drive unit adjacent said sliding unit for reciprocating a test sample, a signal conditioning unit for receiving a plurality of signals from said sliding unit and said reciprocating motion drive unit and a data acquisition and control unit in communication with said signal conditioning unit, said data acquisition and control unit obtaining data from said signal conditioning unit and operatively sending control instructions to said sliding unit and said reciprocating motion drive unit, said sliding unit including an upper plate having a recess for receiving a nose portion of a microscope, a reciprocatable upper sample holder positioned below said upper plate, a lower fixed sample holder positioned below said upper sample plate and a heater unit mounted adjacent said lower fixed sample holder.

2. An improved tribometer, according to claim 1, including a plurality of connectors extending between said upper plate and said lower sample holder, said connectors including a plurality of springs for applying a load between said upper sample holder and said lower sample holder.

3. An improved tribometer, according to claim 2, including a base, wherein said sliding unit is mounted on said base, an insulating plate mounted on said base, a plurality of insulating walls extending upwardly from said insulating plate, said insulating plate and said insulating wall defining a space for receiving said heater unit.

4. An improved tribometer, according to claim 3, including a thermocouple positioned adjacent said lower sample holder, said thermocouple being in communication with said signal conditioning unit.

5. An improved tribometer, according to claim 1, including a base, wherein said sliding unit is mounted on said base, a cover mounted on said base, said base and said cover defining a humidity chamber, a humidity sensor positioned within said humidity chamber, said humidity sensor being in communication with said signal conditioning unit and fluid conduits in communication with said humidity chamber for delivering humidity adjusting fluid to said humidity chamber.

6. An improved tribometer, according to claim 1, including a load sensor for positioning adjacent said lower sample holder, said load sensor being in communication with said signal conditioning unit.

7. An improved tribometer, according to claim 1, including a variable speed electric motor, a drive rod connected to said upper sample holder, said electric motor being operatively connected to said rod for reciprocating said upper sample holder.

8. An improved tribometer, according to claim 7, wherein said reciprocating motion drive unit includes a horizontal support member, opposed walls extending upwardly from said support member, said electric motor being mounted between said opposed walls, a slide plate mounted adjacent the upper ends of said opposed walls, said electric motor being operatively connected to said slide plate, whereby reciprocation of said slide plate reciprocates said upper sample holder.

9. An improved tribometer, according to claim 8, including a bracket connected between said sliding plate and said rod and a load cell mounted in communication with said rod, said load cell sensing the force exerted on the sliding upper test sample by the stationary lower test sample when the upper test sample is moved over the lower test sample, said load cell being in communication with said signal conditioning unit.

10. An improved tribometer, according to claim 8, said electric motor having a horizontal output shaft, a first bevel gear mounted on said output shaft, a crank disk mounted below said slide plate, a vertical shaft extending downwardly from said flywheel, a second bevel gear mounted on said vertical shaft in a mating relationship with said first bevel gear, a cam mounted on said crank disk, said slide plate defining a cam slot generally perpendicular to said opposed walls, said cam slot receiving said cam, whereby said electric motor reciprocates said slide plate and said upper sample holder.

11. An improved tribometer, according to claim 10, wherein said crank disk has an upper surface, said upper surface defining a plurality of openings radially spaced from one another, said cam being mounted in a selected one of said openings.

12. An improved tribometer, according to claim 7, including a speed sensor for measuring the speed of the electric motor, said speed sensor being in communication with said signal conditioning unit.

13. An improved tribometer having a sliding unit for receiving test samples, a reciprocating motion drive unit adjacent said sliding unit for reciprocating a test sample, a signal conditioning unit for receiving a plurality of signals from said sliding unit and said reciprocating motion drive unit and a data acquisition and control unit in communication with said signal conditioning unit, said data acquisition and control unit obtaining data from said signal conditioning unit and operatively sending control instructions to said sliding unit and said reciprocating motion drive unit, a plurality of sensors positioned adjacent said sliding unit and said reciprocating motion drive unit, said sensors being operatively connected to and sending signals to said signal conditioning unit, said signal conditioning unit amplifying and conditioning such sensor signals, said reciprocating motion drive unit including an electric motor, said sliding unit including a heater unit adjacent a test sample, wherein said plurality of sensors includes a thermocouple for sensing the temperature of said test sample and a speed sensor for measuring the speed of said electric motor, said signal conditioning unit including a manual speed controller and a manual temperature controller, a first switch for activating said manual speed controller and sending manual control signals to said electric motor and a second switch for activating said manual temperature controller and sending manual control signals to said heater unit.

14. An improved tribometer, according to claim 13, wherein said data acquisition and control unit includes a first analog to digital board having a plurality of input channels and a second digital to analog board having a plurality of control channels, said first and second boards being operatively connected to said signal conditioning unit, and a computer for mounting said boards, receiving said input signals from said first board and sending control signals to said second board.

15. An improved tribometer having a sliding unit for receiving test samples, a reciprocating motion drive unit adjacent said sliding unit for reciprocating a test sample, a signal conditioning unit for receiving a plurality of signals from said sliding unit and said reciprocating motion drive unit and a data acquisition and control unit in communication with said signal conditioning unit, said data acquisition and control unit obtaining data from said signal conditioning unit and operatively sending control instructions to said sliding unit and said reciprocating motion drive unit, a plurality of sensors position adjacent said sliding unit and said reciprocating motion drive unit, said sensors being operatively connected to and sending signals to said signal conditioning unit, said signal conditioning unit amplifying and conditioning such sensor signals, said reciprocating motion drive unit including an electric motor, said sliding unit including a heater unit adjacent a test sample, wherein said plurality of sensors includes a thermocouple for sensing the temperature of said test sample and a speed sensor for measuring the speed of said electric motor, said signal conditioning unit including a speed controller and a temperature controller, means for activating said speed controller and sending control signals to said electric motor and for activating said temperature controller and sending control signals to said heater unit.

* * * * *